United States Patent
Johnson

(10) Patent No.: US 9,480,620 B2
(45) Date of Patent: Nov. 1, 2016

(54) METHOD AND APPARATUS FOR IMMOBILIZING SUBJECTS UNDERGOING MECHANICAL CPR

(71) Applicant: ZOLL Medical Corporation, Chelmsford, MA (US)

(72) Inventor: Guy R. Johnson, Chelmsford, MA (US)

(73) Assignee: ZOLL MEDICAL CORPORATION, Chelmsford, MA (US)

( * ) Notice: Subject to any disclaimer, the term of this patent is extended or adjusted under 35 U.S.C. 154(b) by 67 days.

(21) Appl. No.: 14/331,082

(22) Filed: Jul. 14, 2014

(65) Prior Publication Data

US 2014/0330176 A1 Nov. 6, 2014

Related U.S. Application Data

(63) Continuation of application No. 13/597,099, filed on Aug. 28, 2012, now Pat. No. 8,777,879.

(51) Int. Cl.
| | |
|---|---|
| *A61H 31/00* | (2006.01) |
| *A61F 5/058* | (2006.01) |
| *A61F 5/37* | (2006.01) |
| *A61H 11/00* | (2006.01) |
| *A61G 13/12* | (2006.01) |

(52) U.S. Cl.
CPC ........... *A61H 31/00* (2013.01); *A61F 5/05833* (2013.01); *A61F 5/3769* (2013.01); *A61H 31/006* (2013.01); *A61H 31/008* (2013.01); *A61G 13/1275* (2013.01); *A61H 2011/005* (2013.01); *A61H 2201/0103* (2013.01); *A61H 2201/0192* (2013.01); *A61H 2201/5071* (2013.01)

(58) Field of Classification Search
CPC .................... A61H 31/006; A61H 2201/5007; A61H 2201/0173; A61H 2011/005; A61H 31/00; A61H 31/008; A61H 2201/0192; A61H 2201/5071; A61F 5/05833; A61F 5/3769; A61G 13/1275
USPC ....... 601/1, 41–44, 89, 93, 90, 97, 103, 104, 601/134, 135, 143, 144, 145; 128/845, 870, 128/877, 874; 602/6, 13, 20; 606/201–203; 264/222
See application file for complete search history.

(56) References Cited

U.S. PATENT DOCUMENTS

| | | | | |
|---|---|---|---|---|
| 4,895,173 | A * | 1/1990 | Brault | A61G 1/044 128/870 |
| 8,777,879 | B2 * | 7/2014 | Johnson | A61H 31/00 128/870 |
| 9,107,800 | B2 * | 8/2015 | Sebelius | A61H 31/008 601/108 |

* cited by examiner

*Primary Examiner* — Steven Douglas
(74) *Attorney, Agent, or Firm* — ZOLL Medical Corporation

(57) ABSTRACT

The apparatus for immobilizing and treating a subject includes a suitable apparatus for performing mechanical CPR secured to an immobilization casing. The airtight flexible casing is secured to the apparatus for performing CPR, the casing having variable rigidity which varies as a function of the amount of air within the casing. Two or more slots through the casing permit passage of one or more elements of the CPR apparatus to pass through the casing. One or more incompressible windows may be included in the casing to optimize the performance of mechanical CPR by permitting one or more elements of the subject's skeleton to contact the CPR apparatus. A device for evacuating the air from within the flexible casing to control the rigidity of the casing is included within the CPR apparatus.

16 Claims, 6 Drawing Sheets

METHOD AND APPARATUS FOR IMMOBILIZING SUBJECTS UNDERGOING MECHANICAL CPR

RELATED APPLICATIONS

This application claims priority from U.S. Utility application Ser. No. 13/597,099 filed Aug. 28, 2012 now U.S. Pat. No. 8,777,879.

FIELD OF THE INVENTIONS

The inventions described below relate to the field of CPR chest compression devices.

BACKGROUND

Cardiopulmonary resuscitation (CPR) is a well-known and valuable method of first aid used to resuscitate people who have suffered from cardiac arrest. CPR requires repetitive chest compressions to squeeze the heart and the thoracic cavity to pump blood through the body. Artificial respiration, such as mouth-to-mouth breathing or a bag mask apparatus, is used to supply air to the lungs. When a first aid provider performs manual chest compression effectively, blood flow in the body is about 25% to 30% of normal blood flow.

In efforts to provide better blood flow and increase the effectiveness of bystander resuscitation efforts, various mechanical devices have been proposed for performing CPR. In one variation of such devices, a belt is placed around the subject's chest and the belt is used to effect chest compressions. Our own patents, Mollenauer et al., Resuscitation device having a motor driven belt to constrict/compress the chest, U.S. Pat. No. 6,142,962 (Nov. 7, 2000); Sherman, et al., CPR Assist Device with Pressure Bladder Feedback, U.S. Pat. No. 6,616,620 (Sep. 9, 2003); Sherman et al., Modular CPR assist device, U.S. Pat. No. 6,066,106 (May 23, 2000); and Sherman et al., Modular CPR assist device, U.S. Pat. No. 6,398,745 (Jun. 4, 2002), and Escudero, et al., Compression Belt System for Use with Chest Compression Devices, U.S. Pat. No. 7,410,470 (Aug. 12, 2008), show chest compression devices that compress a subject's chest with a belt. Our commercial device, sold under the trademark AUTOPULSE®, is described in some detail in our prior patents, including Jensen, Lightweight Electro-Mechanical Chest Compression Device, U.S. Pat. No. 7,347,832 (Mar. 25, 2008) and Quintana, et al., Methods and Devices for Attaching a Belt Cartridge to a Chest Compression Device, U.S. Pat. No. 7,354,407 (Apr. 8, 2008). Each of these patents is hereby incorporated by reference in their entirety.

In some scenarios in which CPR is required to treat cardiac arrest, is it also necessary to immobilize the subject. The subject may have coincident injuries, such as a broken vertebrae or broken hip, that require immobilization. The subject may need to be transported over rugged terrain, up or down stairs, or in sitting or upright positions. In these scenarios, it would be beneficial to provide automated CPR chest compressions while also immobilizing the subject. However, conventional immobilization devices do not work well with available chest compression devices. The components of each device interfere to the extent that they cannot be combined effectively. One example of a desirable immobilization device is illustrated in Koledin, Vacuum Immobilizer Support, U.S. Pat. No. 5,121,756 (Jun. 16, 1992) and Latimer et al., Air Evacuable Support, U.S. Pat. No. 5,154,185 (Oct. 13, 1992) both of which are hereby incorporated by reference in their entirety. These devices comprise bead filled mattresses which, when filled with beads and air, conform to the subject's shape. After placing the subject on the mattress, and allowing the mattress to conform to the subject, the mattress may be evacuated to lock the beads in place and transform the mattress into a rigid backboard which immobilizes the subject.

SUMMARY

The devices and methods described below provide for subject immobilization and simultaneous performance of mechanical CPR. The belt drive platform operates as a generally rigid base that includes all the necessary mechanisms for performing mechanical CPR. The front surface of the platform incorporates an airtight flexible casing partially filled with beads, pellets or other suitable media (or movable discrete elements, in the terminology used in U.S. Pat. No. 5,154,185). When the casing contains enough air to be at or near ambient atmospheric pressure, the casing is flexible and the beads are loose and free to move within the casing or within portions of the casing and conform, or be made to conform, to the shape of the subject lying on the casing. As the air within the casing is evacuated, the beads are forced together into a generally rigid form that has conformed to the subject's body and immobilizes the subject. Slots through the casing enable the ends of the belt for performing mechanical CPR to pass through the casing and encircle the subject's thorax for performance of mechanical CPR. One or more windows in the casing enable skeletal elements of the subject to make contact with the belt drive platform to optimize the resuscitative work of the platform and belt and not waste energy compressing the beads.

A suitable belt drive system includes a belt drive platform that includes a housing and a drive spool operably attached to the housing as well as a means for rotating the drive spool, with the means for rotating disposed within the housing and operably attached to the drive spool. A compression belt cartridge engages the belt drive platform. The compression belt cartridge including the belt suitable for compressing the chest of the subject and a spline attached to the belt, wherein the spline is removably attachable to the drive spool, wherein rotation of the drive spool tightens the belt to compress the chest. An airtight flexible casing is secured to the housing, the casing having variable rigidity which varies as a function of the amount of air within the casing. The casing also includes two or more slots to permit passage of the belt from the drive belt platform to engage the thorax of the subject. A means for evacuating the air from within the flexible casing to control the rigidity of the casing is included within the housing. A plurality of beads are located within the casing, the plurality of beads adapted to move and conform the casing to support the subject to be immobilized when the casing is inflated, the plurality of beads adapted to be rigidly fixed in position when the casing is in a fully evacuated state.

A method for immobilizing and treating a subject requiring CPR includes the steps of providing a mechanical chest compression apparatus and providing an airtight flexible casing secured to the mechanical chest compression apparatus, the casing containing a plurality of beads wherein the beads provide variable rigidity which varies as a function of the amount of air within the casing and providing a vacuum pump for evacuating the air from within the flexible casing to control the rigidity of the casing. A subject requiring CPR is placed on the casing and the beads are arranged to support and immobilize the subject. The subject is secured to the mechanical chest compression apparatus and the air from within the casing is evacuated by the vacuum pump to rigidly compresses plurality of beads and immobilize the subject. The mechanical chest compression apparatus is then activated to repetitively perform chest compressions.

A method for immobilizing and treating a subject requiring CPR includes the steps of providing a mechanical chest compression apparatus and providing an airtight flexible casing secured to the mechanical chest compression apparatus, the casing having at least two independently operable portions, each portion containing a plurality of beads wherein the beads provide variable rigidity which varies as a function of the amount of air within the casing and providing a vacuum pump for evacuating the air from within the independently operable portions of the casing to control the rigidity of the portions of the casing. A subject requiring CPR is placed on the casing and the beads in each portion are arranged to support and immobilize the subject. The subject is secured to the mechanical chest compression apparatus and the air from within one or more portions of the casing is evacuated by the vacuum pump to rigidly compresses plurality of beads in the evacuated portions and immobilize the subject. The mechanical chest compression apparatus is then activated to repetitively perform chest compressions.

DETAILED DESCRIPTION OF THE INVENTIONS

Figure 1:
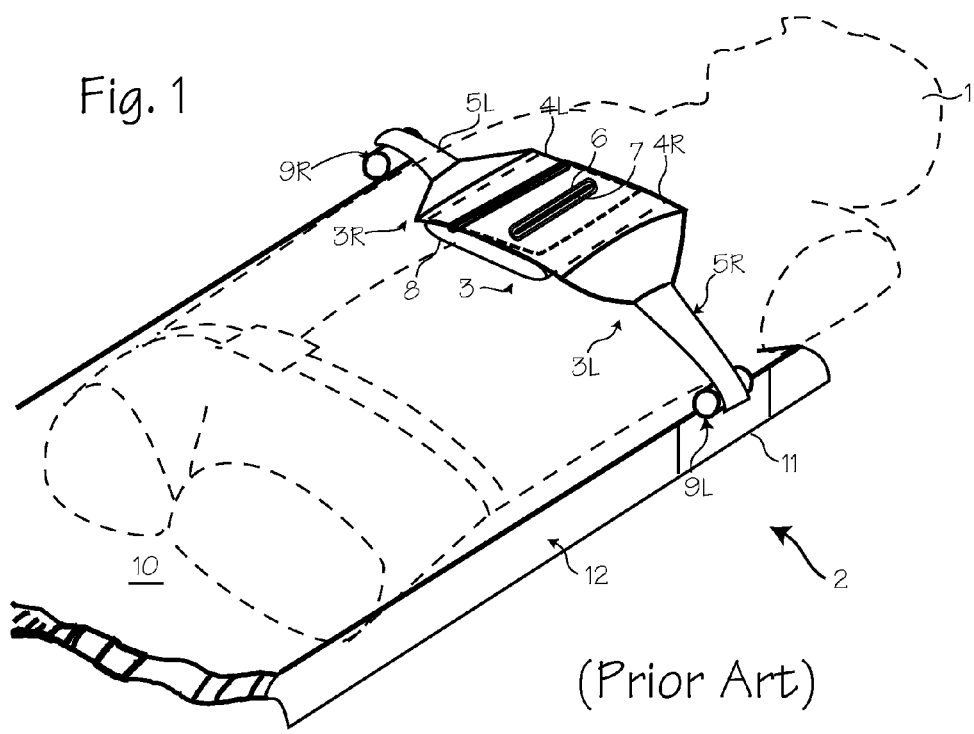
FIG. 1 shows a prior art chest compression belt fitted on a subject.
Figure 2:
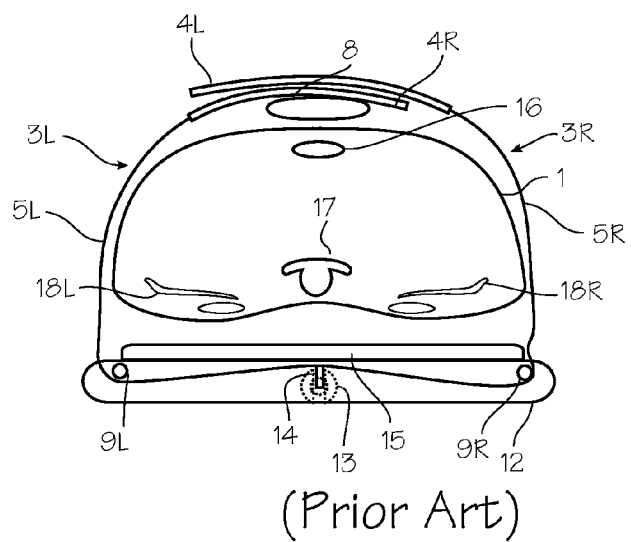
FIG. 2 is a schematic cross section of the chest compression device of FIG. 1.

The apparatus for immobilizing and treating a subject includes a suitable means for mechanically compressing the chest of a subject such as a belt drive compression system, a piston compression system or a vest compression system. A suitable belt drive compression system, similar to the AutoPulse® CPR chest compression device, is illustrated in FIGS. 1 and 2 fitted on a subject 1. Chest compression device 2 applies compressions with the belt 3, which has a right belt portion 3R and a left belt portion 3L, including load distributing panels 4R and 4L designed for placement over the anterior surface of the subject's chest while in use, and tensioning portions which extend from the load distributing portions to a drive spool, shown in the illustration as narrow pull straps 5R and 5L. (The entirety of the compression belt is referred to as a "load distributing band" in the art.) The right belt portion and left belt portion are secured to each other with hook and loop fasteners and aligned with the eyelet 6 and protrusion 7. A bladder 8 is disposed between the belt and the chest of the subject. The narrow pull straps 5R and 5L of the belt are spooled onto a drive spool located within the platform (shown in FIG. 2) to tighten the belt during use, passing first over laterally located spindles 9L and 9R. The chest compression device 2 includes a belt drive platform 10 and a compression belt cartridge 11 (which includes the belt). The platform includes a housing 12 upon which the subject rests. Means for tightening the belt, a processor and a user interface are disposed within the housing. In the commercial embodiment of the device, the means for tightening the belt includes a motor, a drive train (clutch, brake and/or gear box) and a drive spool upon which the belt spools during use.

FIG. 2 is a schematic cross section of the device of FIG. 1, installed on a subject 1. The components include the compression belt 3L and 3R, the load distribution portions of the belt 4L and 4R, the narrow strap portions 5L and 5R, the bladder 8, the spindles 9L and 9R. The drive spool 13 and the spline 14 which fixes the belt to the drive spool are located within the housing 12, as is a motor and computer control system which operate to drive the drive spool to spool the belt, thereby tightening the belt about the chest and thorax of the subject and a resuscitative rate to accomplish CPR. A load plate 15 is disposed on the platform (the upper surface of the housing). The anatomical landmarks shown in this Figure include the sternum 16, the spine 17, and the right and left scapula 18R and 18L of the subject. Referring to the landmarks, the chest compression band is wrapped around the subject such that the load distributing portions are located on the chest (that is, the anterior surface or portion of the thorax), over the sternum, with the narrow strap portions descending from the load distributing portions to wrap around the lateral spindles and thence run to the drive spool. The lateral spindles are spaced laterally from the medial centerline of the device so that they are disposed under, or lateral to, the scapulae of the typical subject, so that tightening of the compression band results in anterior/posterior compression of the chest.

Our experience with mechanical chest compression suggests that the subject must remain in a fixed position relative to the housing: That is, some anatomical parts of the subject must remain in substantially fixed relation to the housing while the sternum is compressed toward the spine. Various other mechanisms or means for chest compression may be used to perform mechanical CPR such as the LUCAS™ chest compression system produced by Physio-Control, Inc. as well as the mechanisms shown in Lach et al., Resuscitation Method and Apparatus, U.S. Pat. No. 4,770,164 (Sep. 13, 1988) and in Kelly et al., Chest Compression Apparatus for Cardiac Arrest, U.S. Pat. No. 5,738,637 (Apr. 14, 1998). The entirety of these patents is hereby incorporated by reference.

Figure 3:
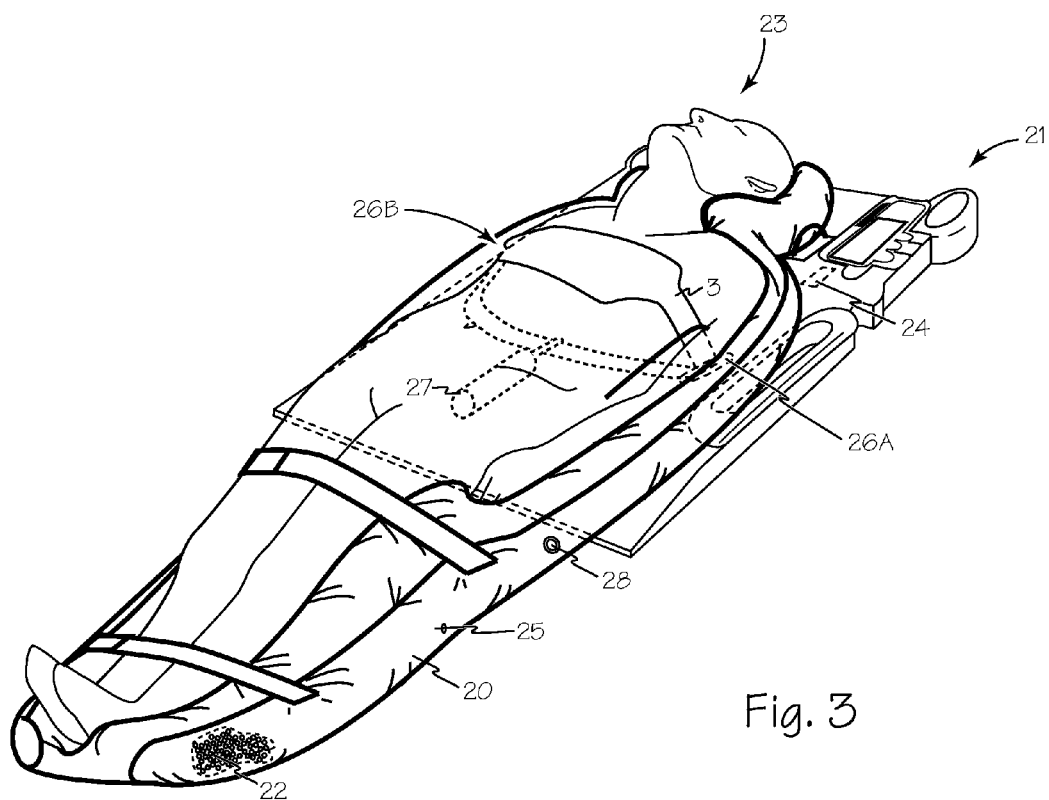
FIG. 3 is a perspective view of a subject immobilized in a full length immobilization casing while also disposed within an automated chest compression device.

Referring now to FIG. 3, an immobilization casing such as full length flexible casing 1920 may be secured to a suitable automated chest compression apparatus such as chest compression device 21. Full length flexible casing 20 may be partially filled with beads 22 to support and immobilize subject 23 as shown in Koledin, Vacuum Immobilizer Support, U.S. Pat. No. 5,121,756 (Jun. 16, 2002) the entirety of which is hereby incorporated by reference. Flexible casings may be available in different sizes to accommodate for example, extra-large, average and small subjects. Vacuum pump 24 is disposed in the housing for controlling the amount of air 25 within the flexible casing and for deflating the flexible casing. Vacuum pump 24 may be any suitable manual or electric means for evacuating the interior of the casing and is in fluid communication with the interior volume of the casing to enable controlled evacuation of the casing to control the rigidity and conformance of the casing and the beads within the casing to the shape of the subject. The combination of rigid immobilization with mechanical CPR or other advanced life support techniques provides help to subjects with multiple problems who would otherwise be impossible to help with conventional immobilization.

The volume of air within flexible casing 20 may also be controlled by valve 28. When a subject is placed on flexible casing 20 the weight of the subject will raise the pressure within the casing and force air 25 out through valve 28. Valve 28 may be any suitable valve to allow air 25 or other fluid to escape from within the casing. Valve 28 may also be used to permit air to reenter casing 20 to permit readjustment of a subject after air 25 has been evacuated.

In use, subject 23 is placed on casing 19 and beads 22 are arranged to support and immobilize the subject and belt portions 3L and 3R are placed through slots 26A and 26B and then under the subject's axilla (armpits), wrapped around the subject's chest, and secured. Vacuum pump 24 is engaged to deflate the casing which rigidly compresses beads 22 together and immobilizes the subject. Means for tightening the belt 27 is activated to tighten belt 3 repetitively to perform chest compressions.

Figure 4:
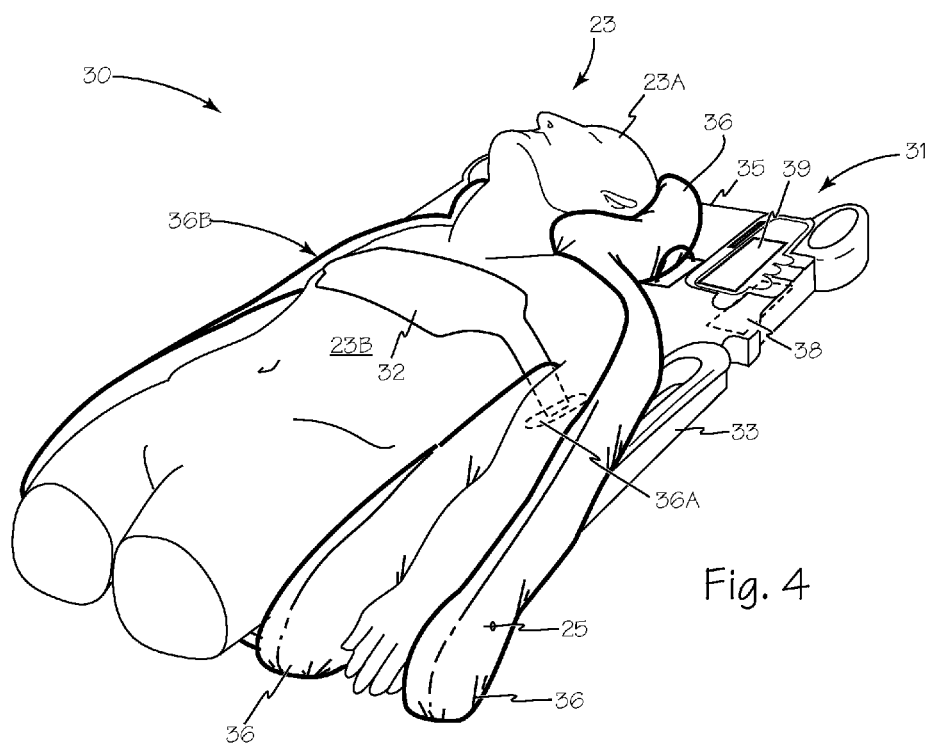
FIG. 4 is a perspective view of a subject immobilized in an upper body immobilization casing while also disposed within an automated chest compression device.
Figure 5:
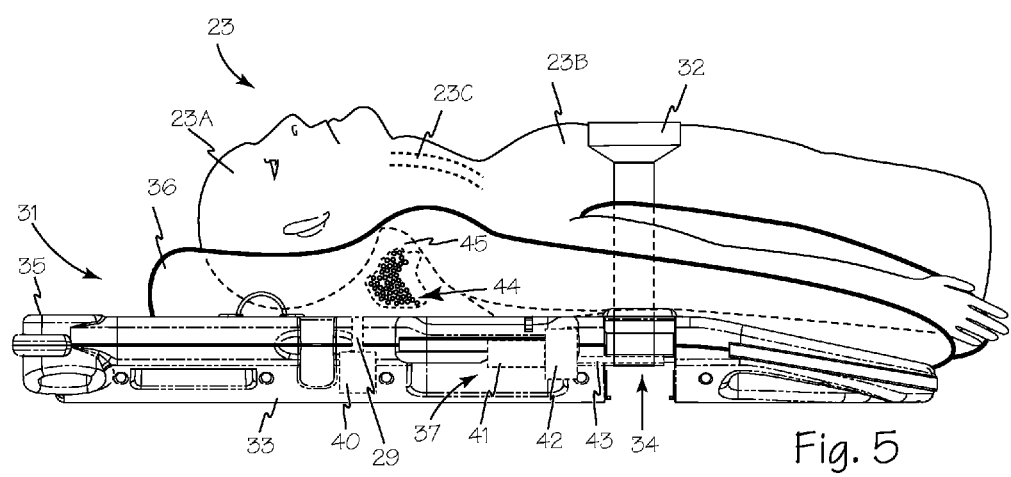
FIG. 5 is a side view of the subject and apparatus of FIG. 4.

Resuscitation apparatus 30 of FIGS. 4 and 5 includes any suitable chest compression device such as chest compression device 31 which applies compressions with the belt 32. The chest compression device 31 includes a belt drive platform 33 and a compression belt cartridge 34 (which includes the belt 32). The belt drive platform includes a housing 35 engaging an upper body airtight flexible casing 36 upon which subject 23 rests and is immobilized, a means 37 for tightening the belt, a processor 38, a user interface 39 and a vacuum pump 40 such as a vacuum pump disposed in the housing for controlling the amount of air 25 within the flexible casing and for deflating the flexible casing. Flexible casing 36 is partially filled with movable, discrete elements such as beads or pellets 44 to support and immobilize the subject. Pellets 44 may be made of expanded or solid plastic material, such as polystyrene or polyvinyl chloride and be formed in any shape such as spherical or other suitable regular or irregular shape. The loose beads or pellets within an inflated flexible casing permit the casing sides to be moved up against the sides of the subject to cradle and support the subject. The beads are then movable to conform to the contours of the patient's body, and also movable to regions where greater rigidity is required.

Additionally, casing 36 may also include one or more portions that may be independently operable as well as containing specific quantities of pellets 44 in each portion to control the profile and rigidity of the independent portions. For example, neck wedge portion 45 may be configured with pellets 44 to maintain alignment between the subject's head 23A and the subject's thorax 23B with the subject's airway 23C optimally opened as illustrated. Independent operability of the one or more portions of a casing may be accomplished using multiple vacuum pumps independently controllable by processor 38, or a singe vacuum pump with a valving system controllable by processor 38. Means for tightening the belt 37 includes a motor 41, a drive train 42 (clutch, brake and/or gear box) and a drive spool 43 upon which the belt spools during use.

Processor 38 is operably connected to vacuum pump 40 to control the rigidity of casing 36 and one or more vacuum or pressure sensor such as sensor 29 to monitor and provide feedback to the processor. Sensor 29 may be operably connected to casing 36 or vacuum pump 40 to monitor the pressure (vacuum) within the casing and therefore its rigidity. Processor 38 may include one or more preset pressure settings for the casing and for each separate portion of the casing. Sensor 29 may also provide feedback to rescuers when manually controlling the operation of the vacuum pump or manually pumping air from the casing.

Figure 6:
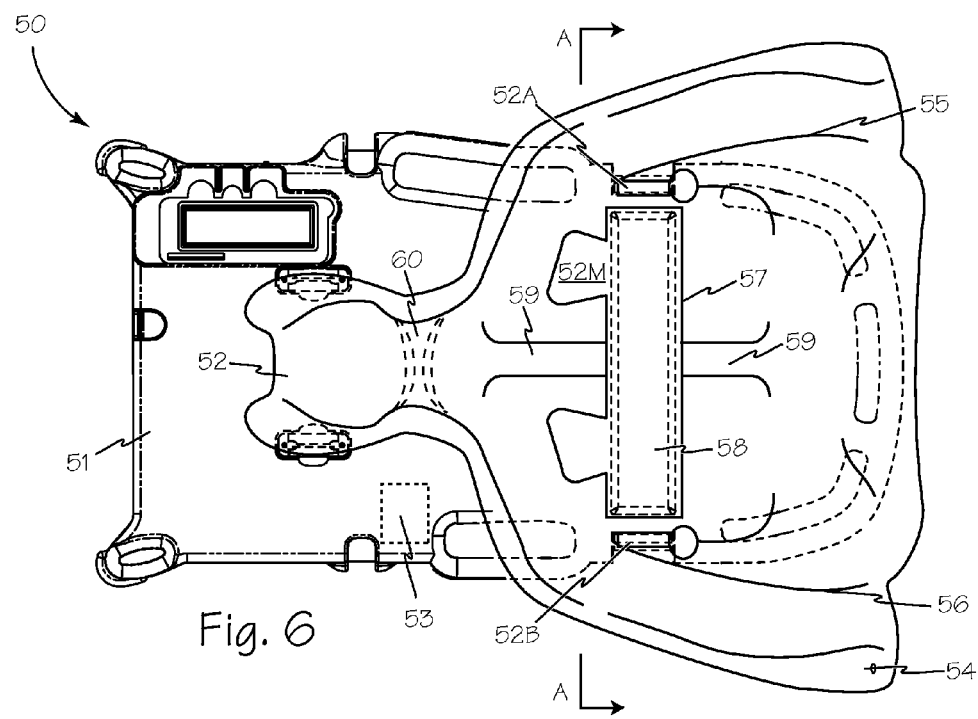
FIG. 6 is a top view of the automatic chest compression device of FIG. 4.
Figure 7:
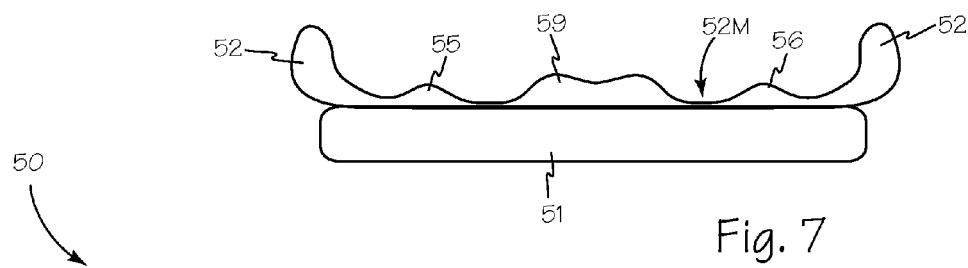
FIG. 7 is a cross-section view of the apparatus of FIG. 6 taken along A-A.
Figure 8:
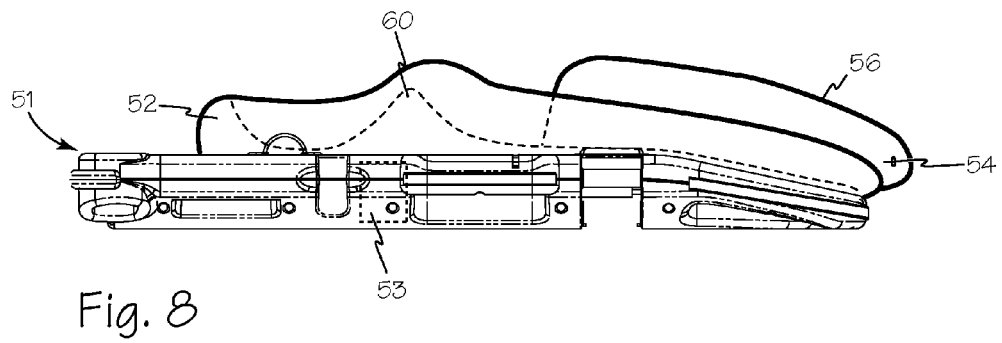
FIG. 8 is a side view of the apparatus of FIG. 6.

Referring now to FIGS. 6, 7 and 8, rescue apparatus 50 includes an automated CPR apparatus such as belt drive platform 51 secured to an upper body airtight flexible casing such as casing 52 secured to housing. Casing 52 is in fluid communication with vacuum pump 53 which controls the amount of air 54 within casing 52. Casing 52 is sized to support a subject from the head to the waist and it includes ridges such as first ridge 55 and second ridge 56 which provide separation between the subject's arms and the subject's thorax when the subject is immobilized. Within support ridges 55 and 56 are one or more slots or openings such as slots 52A and 52B respectively. The openings or slots permit a compression belt or compression support structure to pass through the casing to enable mechanical CPR to be performed on an immobilized subject. The casing may also include a neck support portion of the casing to maintain alignment between the subject's head and torso and open the subject's airway.

To provide optimal compression of the subject's thorax, one or more windows are provided in casing such as scapular window 57 which are oriented to conform to the scapulae of a subject properly oriented on the automated chest compression device. The windows are areas of the casing that are sealed to prevent entry of any beads 22 into the window space. This configuration has only one or more layers of incompressible casing material 52M between the subject's scapulae and belt drive platform 51. This configuration enables the chest compression device to compress the subject's chest without compressing the beads within the immobilizing casing. One or more incompressible windows may also be provided to expose load sensors, such as load sensor 58, to the subject's weight and the compression force without any beads between the subject and the load sensor or sensors. The load sensors are operably connected to the any suitable chest compression means for controlling the intensity of the chest compressions. One or more support sections may be included to maintain alignment and immobilization of the subject's skeleton during CPR such as spinal support section 59.

Casing 52 may also include one or more portions that may be have independent air content controls as well as specific quantities of beads 22 to control the profile of the independent portions such as spinal support section 59, neck wedge 60 and or first and second ridges 55 and 56 respectively. Independent control enables the head and neck of a subject to be immobilized for performance of intubation separately from thorax or torso immobilization. Alternatively, the separate casings may be maintained at different levels of rigidity to accommodate the specific injuries of the subject.

Figure 9:
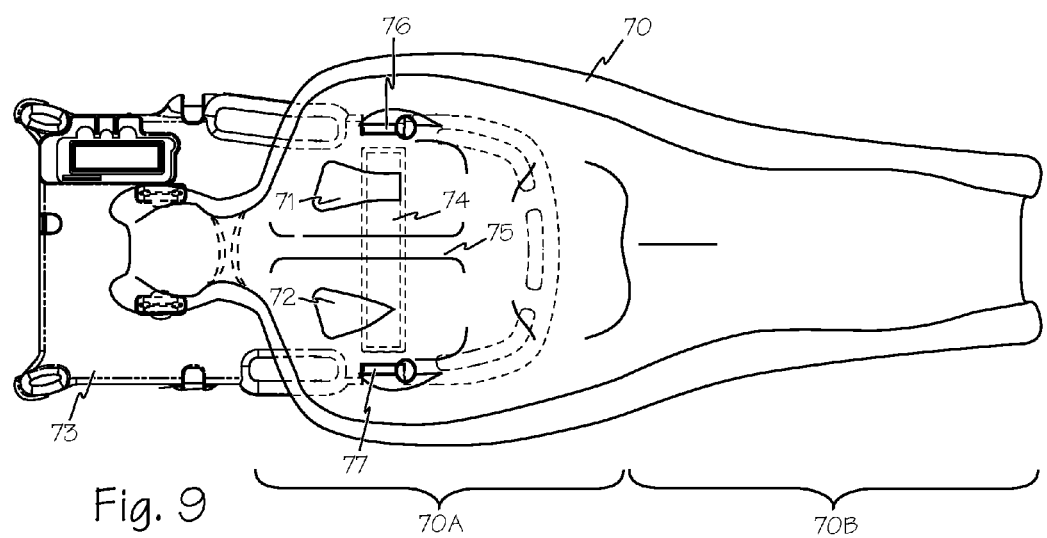
FIG. 9 is a top view of the automatic chest compression device with a full size immobilizer casing.
Figure 10:
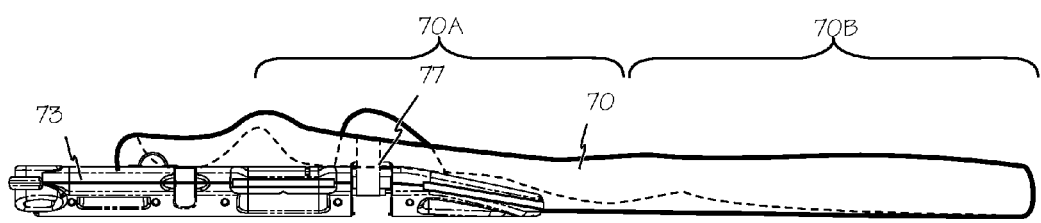
FIG. 10 is a side view of the apparatus of FIG. 9.

Referring now to FIGS. 9 and 10, full size casing 70 is configured to secure a subject's arms to the side of the body with minimal separation between the arms and the body in torso portion 70A as well as the full length of the subject's legs and feet with leg portion 70B. Scapular windows such as first scapular window 71 and second scapular window 72 are oriented to permit a subject's scapula to contact belt drive platform 73 and one or more load sensors such as load sensor 74. Scapular windows such as scapular windows 71 and 72 may adopt any suitable configuration such as the scapular specific shape of second scapular window 72 or a shape such as first scapular window 71 to optimize contact between the subject's body and load sensor 74. The configuration of casing 70 also includes a full length spinal support 75 and first and second slots 76 and 77 respectively to provide access for belts or support frames for automated CPR devices.

Figure 11:
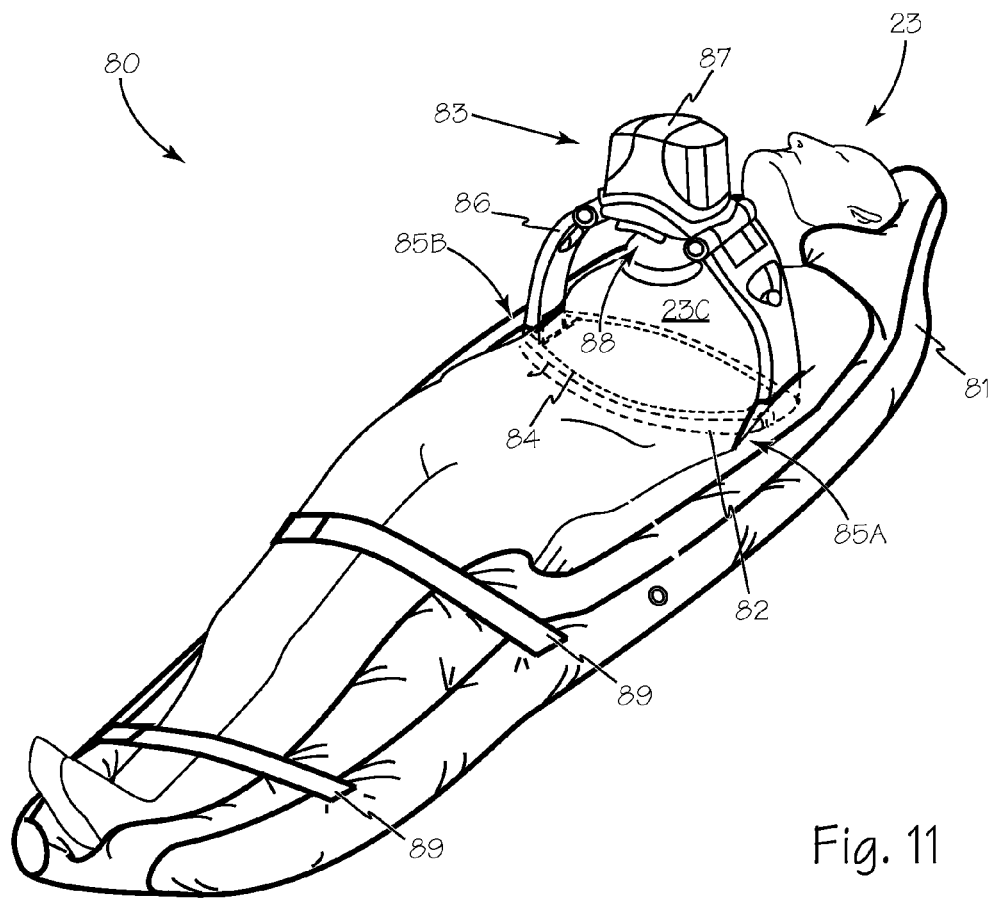
FIG. 11 is a perspective view of a subject immobilized in a full length immobilization casing while also disposed within an automated chest compression device.

Referring now to FIG. 11, immobilization and rescue apparatus 80 includes full length immobilization casing 81 connected to backboard 82 of LUCAS™ chest compression system 83. As discussed above, casing 81 may also be a torso only immobilizer and may include one or more windows such as window 84 to permit skeletal elements of subject 23 to contact backboard 82 with no intervening compressible elements. Window 84 will be formed in casing 81 in the area generally supporting the scapulae and the area between the scapulae of a subject properly oriented in the casing. Casings such as casing 81 include one or more access slots or holes such as slots 85A and 85B to permit support structure such as support legs 86 to pass through the immobilization casing and support chest compression unit 87 with piston 88 apposing subject's chest 23C. The casing may also include one or more restraining straps 89 to further engage and immobilize subject 23.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

I claim:

1. An apparatus for immobilizing and treating a subject comprising: a piston compression system for repetitively compressing the chest of a subject with a chest compression unit driving a piston, the chest compression unit is supported by at least two legs secured to a backboard with the piston apposing the subject's chest; an airtight flexible casing secured to the backboard, the casing containing air and having two or more slots to permit passage of the at least two legs of the chest compression unit through the casing wherein the casing has a variable rigidity which varies as a function of the amount of air within the casing; a vacuum pump for evacuating the air from within the airtight flexible casing to control a rigidity of the casing; a plurality of beads located within the casing, the plurality of beads adapted to move and conform the casing to support the subject when the casing contains air, the plurality of beads adapted to be rigidly fixed in position when the casing is in a fully evacuated state.

2. The apparatus of claim 1 further comprising:
two separation ridges formed in the casing, each separation ridge separating one of the subject's arms from the subject's torso.

3. The apparatus of claim 2 further comprising:
a scapular window sealed in the casing, the scapular window containing no beads to enable contact between the subject's scapula and the backboard.

4. The apparatus of claim 3 further comprising:
a neck support configured in the casing to maintain alignment between the subject's head and torso and open the subject's airway.

5. The apparatus of claim 3 wherein the airtight flexible casing supports and immobilizes the subject from head to foot.

6. The apparatus of claim 3 wherein the airtight flexible casing supports and immobilizes the subject from head to waist.

7. The apparatus of claim 3 wherein the casing further comprises:
two or more portions, wherein each portion of the two or more portions is independently operable to control a profile and rigidity of each portion of the two or more portions.

8. The apparatus of claim 7 wherein one of the two or more portions comprises: a neck support configured in the casing to maintain alignment between the subject's head and torso and open the subject's airway.

9. The apparatus of claim 1 further comprising:
a processor, the processor controlling the operation of the vacuum pump to control the rigidity of the casing.

10. The apparatus of claim 9 further comprising:
a sensor operably connected to the processor for measuring pressure within the casing to enable the processor to control the operation of the vacuum pump to control the rigidity of the casing.

11. The apparatus of claim 7 further comprising:
a processor, the processor controlling the operation of the vacuum pump to independently control the rigidity of the two or more portions of the casing.

12. The apparatus of claim 1 further comprising: a valve in fluid communication with air in the casing to permit the air to leave the casing when the subject is placed on the casing.

13. The apparatus of claim 3 further comprising: a load sensor secured to the backboard between the scapular window and the backboard, the load sensor operably connected to the chest compression unit.

14. A method for immobilizing and treating a subject comprising the steps:
providing a means for mechanically compressing the chest of the subject; providing an airtight flexible casing secured to the means for mechanically compressing the chest of the subject, the casing having at least two independently operable portions, each portion containing air and a plurality of beads wherein the beads provide variable rigidity which varies as a function of the amount of air within the portion of the casing; providing a vacuum pump for evacuating the air from within the at least two independently operable portions of the casing to control the rigidity of each portion of the casing; placing the subject on the casing; arranging the plurality of beads in the at least two independently operable portions of the casing to support and immobilize the subject; securing a subject to the means for mechanically compressing the chest of the subject; evacuating the air from within one or more of the at least two independently operable portions of the casing to rigidly compress the plurality of beads in the one or more evacuated portions and immobilize the subject; and activating the means for mechanically compressing the chest to repetitively perform chest compressions.

15. The method of claim 14 wherein the step of evacuating the air from within the one or more of the at least two independently operable portions of the casing further comprises operating the vacuum pump to evacuate a portion of the air from within the one or more of the at least two independently operable portions of the casing to compress the plurality of beads in the one or more of the at least two independently operable portions of the casing to a preset level of rigidity.

16. The method of claim 14 further comprising the step:
  measuring the force of mechanical chest compressions using one or more force sensors between the means for mechanically compressing the chest and the casing.

\* \* \* \* \*